(12) United States Patent
Alamin et al.

(10) Patent No.: US 10,080,589 B2
(45) Date of Patent: Sep. 25, 2018

(54) METHODS AND SYSTEMS FOR CONSTRAINT OF SPINOUS PROCESSES WITH ATTACHMENT

(71) Applicants: The Board of Trustees of the Leland Stanford Junior University, Stanford, CA (US); Empirical Spine, Inc., Woodside, CA (US)

(72) Inventors: Todd Alamin, Woodside, CA (US); Ian Bennett, San Francisco, CA (US); Louis Fielding, Portland, OR (US); Colin Cahill, San Francisco, CA (US)

(73) Assignees: The Board of Trustees of the Leland Stanford Junior University, Stanford, CA (US); Empirical Spine, Inc., Woodside, CA (US)

(*) Notice: Subject to any disclaimer, the term of this patent is extended or adjusted under 35 U.S.C. 154(b) by 0 days.

(21) Appl. No.: 15/409,436

(22) Filed: Jan. 18, 2017

(65) Prior Publication Data
US 2017/0319242 A1    Nov. 9, 2017

Related U.S. Application Data

(63) Continuation of application No. 14/875,495, filed on Oct. 5, 2015, now abandoned, which is a continuation
(Continued)

(51) Int. Cl.
*A61B 17/70* (2006.01)
*A61B 17/84* (2006.01)
(Continued)

(52) U.S. Cl.
CPC ...... *A61B 17/7067* (2013.01); *A61B 17/7053* (2013.01); *A61B 17/7055* (2013.01);
(Continued)

(58) Field of Classification Search
CPC .. A61B 17/70; A61B 17/7062; A61B 17/7053
See application file for complete search history.

(56) References Cited

U.S. PATENT DOCUMENTS

| 3,648,691 A | 3/1972 | Lumb et al. |
| 4,246,660 A | 1/1981 | Wevers |

(Continued)

FOREIGN PATENT DOCUMENTS

| EP | 0322334 A1 | 6/1989 |
| EP | 0743045 A2 | 11/1996 |

(Continued)

OTHER PUBLICATIONS

Abbott Spine; Wallis Surgical Technique; The Art & Science of Spine Surgery; Product brochure; 22 pgs.; (year of pub. sufficiently earlier than effective US filed and any foreign priority date) 2006.
(Continued)

*Primary Examiner* — Christopher Beccia
(74) *Attorney, Agent, or Firm* — Shay Glenn LLP

(57) ABSTRACT

Spinal implants for limiting flexion of the spine are implanted between a superior spinous process and an inferior spinous process or sacrum. The implants include upper straps which are placed over the upper spinous process, while the lower portions of the implant are attached to the adjacent vertebra or sacrum. The attachments may be fixed, for example using screws or other anchors, or may be non-fixed, for example by placing a loop strap through a hole in the spinous process or sacrum.

10 Claims, 10 Drawing Sheets

Related U.S. Application Data of application No. 13/958,323, filed on Aug. 2, 2013, now Pat. No. 9,149,304, which is a continuation of application No. 11/827,980, filed on Jul. 13, 2007, now Pat. No. 8,523,904, which is a continuation-in-part of application No. 11/076,469, filed on Mar. 9, 2005, now Pat. No. 7,458,981.

(60) Provisional application No. 60/862,085, filed on Oct. 19, 2006, provisional application No. 60/551,235, filed on Mar. 9, 2004.

(51) Int. Cl.
*A61B 17/00* (2006.01)
*A61B 17/68* (2006.01)
*A61B 17/04* (2006.01)

(52) U.S. Cl.
CPC ........ *A61B 17/7062* (2013.01); *A61B 17/842* (2013.01); *A61B 17/846* (2013.01); *A61B 17/683* (2013.01); *A61B 2017/00862* (2013.01); *A61B 2017/0417* (2013.01); *A61B 2017/7073* (2013.01)

(56) References Cited

U.S. PATENT DOCUMENTS

| | | | |
|---|---|---|---|
| 4,643,178 | A | 2/1987 | Nastari et al. |
| 4,708,132 | A | 11/1987 | Silvestrini |
| 4,743,260 | A | 5/1988 | Burton |
| 4,772,286 | A | 9/1988 | Goble et al. |
| 4,773,402 | A | 9/1988 | Asher et al. |
| 4,776,851 | A | 10/1988 | Bruchman et al. |
| 4,794,916 | A | 1/1989 | Porterfield et al. |
| 4,870,957 | A | 10/1989 | Goble et al. |
| 4,955,910 | A | 9/1990 | Bolesky |
| 4,966,600 | A | 10/1990 | Songer et al. |
| 4,998,936 | A | 3/1991 | Mehdian |
| 5,002,574 | A | 3/1991 | May et al. |
| 5,011,484 | A | 4/1991 | Breard |
| 5,011,494 | A | 4/1991 | Von Recum et al. |
| 5,030,220 | A * | 7/1991 | Howland ............ A61B 17/7011 606/261 |
| 5,092,866 | A | 3/1992 | Breard et al. |
| 5,108,433 | A | 4/1992 | May et al. |
| 5,116,340 | A | 5/1992 | Songer et al. |
| 5,171,280 | A | 12/1992 | Baumgartner |
| 5,180,393 | A | 1/1993 | Commarmond |
| 5,282,863 | A | 2/1994 | Burton |
| 5,354,917 | A | 10/1994 | Sanderson et al. |
| 5,366,455 | A | 11/1994 | Dove et al. |
| 5,387,213 | A | 2/1995 | Breard et al. |
| 5,395,374 | A | 3/1995 | Miller et al. |
| 5,415,658 | A | 5/1995 | Kilpela et al. |
| 5,415,661 | A | 5/1995 | Holmes |
| 5,449,361 | A | 9/1995 | Preissman |
| 5,456,722 | A | 10/1995 | McLeod et al. |
| 5,458,601 | A | 10/1995 | Young, Jr. et al. |
| 5,462,542 | A | 10/1995 | Alesi, Jr. |
| 5,496,318 | A | 3/1996 | Howland et al. |
| 5,540,698 | A | 7/1996 | Preissman |
| 5,562,653 | A | 10/1996 | Thompson |
| 5,562,737 | A | 10/1996 | Graf |
| 5,593,407 | A | 1/1997 | Reis |
| 5,609,634 | A | 3/1997 | Voydeville |
| 5,628,756 | A | 5/1997 | Barker, Jr. et al. |
| 5,645,084 | A | 7/1997 | McKay |
| 5,645,599 | A | 7/1997 | Samani |
| 5,669,917 | A | 9/1997 | Sauer et al. |
| 5,672,175 | A | 9/1997 | Martin |
| 5,707,379 | A | 1/1998 | Fleenor et al. |
| 5,725,582 | A | 3/1998 | Bevan et al. |
| 5,810,815 | A | 9/1998 | Morales |
| 5,836,948 | A | 11/1998 | Zucherman et al. |
| 5,902,305 | A | 5/1999 | Beger et al. |
| RE36,221 | E | 6/1999 | Breard et al. |
| 5,928,232 | A | 7/1999 | Howland et al. |
| 5,933,452 | A | 8/1999 | Eun |
| 5,935,133 | A | 8/1999 | Wagner et al. |
| 5,964,769 | A | 10/1999 | Wagner et al. |
| 5,989,256 | A | 11/1999 | Kuslich et al. |
| 6,053,921 | A | 4/2000 | Wagner et al. |
| 6,193,721 | B1 | 2/2001 | Michelson |
| 6,224,630 | B1 | 5/2001 | Bao et al. |
| 6,248,106 | B1 | 6/2001 | Ferree |
| 6,283,996 | B1 | 9/2001 | Chervitz et al. |
| 6,287,308 | B1 | 9/2001 | Betz et al. |
| 6,290,724 | B1 | 9/2001 | Marino |
| 6,296,643 | B1 | 10/2001 | Hopf et al. |
| 6,312,431 | B1 | 11/2001 | Asfora |
| 6,322,279 | B1 | 11/2001 | Yamamoto et al. |
| 6,364,883 | B1 | 4/2002 | Santilli |
| 6,378,289 | B1 | 4/2002 | Trudeau et al. |
| 6,391,030 | B1 | 5/2002 | Wagner et al. |
| 6,395,018 | B1 | 5/2002 | Castaneda |
| 6,427,080 | B1 | 7/2002 | Radak |
| 6,436,099 | B1 | 8/2002 | Drewry et al. |
| 6,451,019 | B1 | 9/2002 | Zucherman et al. |
| 6,468,309 | B1 | 10/2002 | Lieberman |
| 6,488,683 | B2 * | 12/2002 | Lieberman ............ A61B 17/70 606/263 |
| 6,517,578 | B2 | 2/2003 | Hein |
| 6,558,389 | B2 | 5/2003 | Clark et al. |
| 6,582,433 | B2 | 6/2003 | Yun |
| 6,589,246 | B1 | 7/2003 | Hack et al. |
| 6,605,091 | B1 | 8/2003 | Iwanski |
| 6,616,669 | B2 | 9/2003 | Ogilvie et al. |
| 6,626,944 | B1 | 9/2003 | Taylor |
| 6,629,975 | B1 | 10/2003 | Kilpela et al. |
| 6,652,527 | B2 | 11/2003 | Zucherman et al. |
| 6,652,585 | B2 | 11/2003 | Lange |
| 6,656,185 | B2 | 12/2003 | Gleason et al. |
| 6,669,729 | B2 | 12/2003 | Chin |
| 6,682,533 | B1 | 1/2004 | Dinsdale et al. |
| 6,689,140 | B2 | 2/2004 | Cohen |
| 6,689,168 | B2 | 2/2004 | Lieberman |
| 6,695,852 | B2 | 2/2004 | Gleason |
| 6,712,819 | B2 | 3/2004 | Zucherman et al. |
| 6,716,245 | B2 | 4/2004 | Pasquet et al. |
| 6,761,720 | B1 | 7/2004 | Senegas |
| 6,828,357 | B1 | 12/2004 | Martin et al. |
| 6,835,205 | B2 * | 12/2004 | Atkinson ............... A61B 17/70 623/17.11 |
| 6,899,716 | B2 | 5/2005 | Cragg |
| 6,989,011 | B2 | 1/2006 | Paul et al. |
| 7,029,475 | B2 | 4/2006 | Panjabi |
| 7,163,558 | B2 | 1/2007 | Senegas et al. |
| 7,201,751 | B2 | 4/2007 | Zucherman et al. |
| 7,229,441 | B2 | 6/2007 | Trieu et al. |
| 7,335,203 | B2 | 2/2008 | Winslow et al. |
| 7,413,576 | B2 | 8/2008 | Sybert et al. |
| 7,452,351 | B2 | 11/2008 | Miller et al. |
| 7,458,981 | B2 | 12/2008 | Fielding et al. |
| 7,520,887 | B2 | 4/2009 | Maxy et al. |
| 7,524,324 | B2 | 4/2009 | Winslow et al. |
| 7,553,320 | B2 | 6/2009 | Molz, IV et al. |
| 7,591,837 | B2 | 9/2009 | Goldsmith |
| 7,837,711 | B2 | 11/2010 | Bruneau et al. |
| 8,029,541 | B2 | 10/2011 | Alamin et al. |
| 8,029,549 | B2 | 10/2011 | Malandain et al. |
| 8,105,363 | B2 | 1/2012 | Fielding et al. |
| 8,114,135 | B2 | 2/2012 | Malandain |
| 8,216,275 | B2 | 7/2012 | Fielding et al. |
| 8,454,660 | B2 | 6/2013 | Alamin et al. |
| 8,486,110 | B2 | 7/2013 | Fielding et al. |
| 8,523,904 | B2 | 9/2013 | Alamin et al. |
| 8,529,606 | B2 | 9/2013 | Alamin et al. |
| 8,920,473 | B2 | 12/2014 | Trautwein et al. |
| 9,149,304 | B2 | 10/2015 | Alamin et al. |
| 9,295,499 | B2 | 3/2016 | Alamin et al. |
| 2001/0007073 | A1 | 7/2001 | Zucherman et al. |
| 2002/0151978 | A1 | 10/2002 | Zacouto et al. |
| 2002/0161446 | A1 | 10/2002 | Bryan et al. |

(56) References Cited

U.S. PATENT DOCUMENTS

| | | |
|---|---|---|
| 2003/0023241 A1 | 1/2003 | Drewry et al. |
| 2003/0050700 A1 | 3/2003 | Kihara |
| 2003/0088251 A1 | 5/2003 | Braun et al. |
| 2003/0153914 A1 | 8/2003 | Oribe et al. |
| 2004/0024458 A1 | 2/2004 | Senegas et al. |
| 2004/0034351 A1 | 2/2004 | Sherman et al. |
| 2004/0082954 A1 | 4/2004 | Teitelbaum et al. |
| 2004/0106995 A1 | 6/2004 | Le Couedic et al. |
| 2004/0116927 A1 | 6/2004 | Graf |
| 2004/0117017 A1 | 6/2004 | Pasquet et al. |
| 2004/0127989 A1 | 7/2004 | Dooris et al. |
| 2004/0143268 A1 | 7/2004 | Falahee |
| 2004/0167520 A1 | 8/2004 | Zucherman et al. |
| 2004/0172132 A1 | 9/2004 | Ginn |
| 2004/0243239 A1 | 12/2004 | Taylor |
| 2005/0033435 A1 | 2/2005 | Belliard et al. |
| 2005/0049708 A1 | 3/2005 | Atkinson et al. |
| 2005/0123581 A1 | 6/2005 | Ringeisen et al. |
| 2005/0154390 A1 | 7/2005 | Biedermann et al. |
| 2005/0192581 A1* | 9/2005 | Molz ............... A61B 17/842 606/74 |
| 2005/0203514 A1 | 9/2005 | Jahng et al. |
| 2005/0203624 A1 | 9/2005 | Serhan et al. |
| 2005/0228383 A1 | 10/2005 | Zucherman et al. |
| 2005/0267470 A1 | 12/2005 | McBride |
| 2005/0267518 A1 | 12/2005 | Wright et al. |
| 2006/0036324 A1 | 2/2006 | Sachs et al. |
| 2006/0041259 A1 | 2/2006 | Paul et al. |
| 2006/0064166 A1 | 3/2006 | Zucherman et al. |
| 2006/0069447 A1 | 3/2006 | DiSilvestro et al. |
| 2006/0084976 A1 | 4/2006 | Borgstrom et al. |
| 2006/0106381 A1 | 5/2006 | Ferree et al. |
| 2006/0106397 A1 | 5/2006 | Lins |
| 2006/0136060 A1 | 6/2006 | Taylor |
| 2006/0142760 A1 | 6/2006 | McDonnell et al. |
| 2006/0149278 A1 | 7/2006 | Kwak et al. |
| 2006/0195102 A1 | 8/2006 | Malandain |
| 2006/0240533 A1 | 10/2006 | Sengupta et al. |
| 2006/0241591 A1 | 10/2006 | Biscup et al. |
| 2006/0241610 A1 | 10/2006 | Lim et al. |
| 2006/0241614 A1 | 10/2006 | Bruneau et al. |
| 2006/0271055 A1 | 11/2006 | Thramann |
| 2007/0010822 A1 | 1/2007 | Zalenski et al. |
| 2007/0073293 A1 | 3/2007 | Martz et al. |
| 2007/0083200 A1 | 4/2007 | Gittings et al. |
| 2007/0173818 A1 | 7/2007 | Hestad et al. |
| 2007/0213829 A1 | 9/2007 | Le Couedic et al. |
| 2007/0233096 A1 | 10/2007 | Garcia-Bengochea |
| 2007/0270827 A1 | 11/2007 | Lim et al. |
| 2007/0270828 A1 | 11/2007 | Bruneau et al. |
| 2007/0299445 A1 | 12/2007 | Shadduck et al. |
| 2008/0021466 A1 | 1/2008 | Shadduck et al. |
| 2008/0027435 A1 | 1/2008 | Zucherman et al. |
| 2008/0033552 A1 | 2/2008 | Lee et al. |
| 2008/0045949 A1 | 2/2008 | Hunt et al. |
| 2008/0051784 A1 | 2/2008 | Gollogly |
| 2008/0097431 A1 | 4/2008 | Vessa |
| 2008/0108993 A1 | 5/2008 | Bennett et al. |
| 2008/0114357 A1 | 5/2008 | Allard et al. |
| 2008/0125780 A1 | 5/2008 | Feree |
| 2008/0177298 A1 | 7/2008 | Zucherman et al. |
| 2008/0183209 A1 | 7/2008 | Robinson et al. |
| 2008/0234736 A1 | 9/2008 | Trieu et al. |
| 2008/0262549 A1 | 10/2008 | Bennett et al. |
| 2008/0281423 A1 | 11/2008 | Sheffer et al. |
| 2008/0294200 A1 | 11/2008 | Kohm et al. |
| 2008/0312693 A1 | 12/2008 | Trautwein et al. |
| 2008/0319487 A1 | 12/2008 | Fielding et al. |
| 2009/0030457 A1 | 1/2009 | Janowski et al. |
| 2009/0118766 A1 | 5/2009 | Park et al. |
| 2009/0264929 A1 | 10/2009 | Alamin et al. |
| 2009/0264932 A1 | 10/2009 | Alamin et al. |
| 2009/0270918 A1 | 10/2009 | Attia et al. |
| 2009/0292314 A1 | 11/2009 | Mangione et al. |
| 2010/0004701 A1 | 1/2010 | Malandain et al. |
| 2010/0023060 A1 | 1/2010 | Bennett et al. |
| 2010/0036424 A1 | 2/2010 | Fielding et al. |
| 2010/0234890 A1 | 9/2010 | Alamin et al. |
| 2010/0234894 A1 | 9/2010 | Alamin et al. |
| 2010/0249839 A1 | 9/2010 | Alamin et al. |
| 2010/0274285 A1 | 10/2010 | Rouleau |
| 2011/0238114 A1 | 9/2011 | Lim et al. |
| 2012/0165872 A1 | 6/2012 | Alamin et al. |
| 2012/0184998 A1 | 7/2012 | Alamin et al. |
| 2012/0209328 A1 | 8/2012 | Alamin et al. |
| 2016/0008038 A1 | 1/2016 | Alamin et al. |
| 2016/0175016 A1 | 6/2016 | Alamin et al. |
| 2016/0256201 A1 | 9/2016 | Alamin et al. |
| 2017/0231667 A1 | 8/2017 | Alamin et al. |

FOREIGN PATENT DOCUMENTS

| | | |
|---|---|---|
| EP | 0743045 A3 | 12/1996 |
| EP | 0873718 A2 | 10/1998 |
| EP | 1994901 A1 | 11/2008 |
| FR | 2681525 A1 | 3/1993 |
| FR | 2693364 A1 | 1/1994 |
| FR | 2703239 A1 | 10/1994 |
| FR | 2704745 A1 | 11/1994 |
| FR | 2714591 A1 | 7/1995 |
| FR | 2717675 A1 | 9/1995 |
| FR | 2722980 A1 | 2/1996 |
| FR | 2844179 A1 | 3/2004 |
| FR | 2851154 A1 | 8/2004 |
| FR | 2874167 A1 | 2/2006 |
| FR | 2884136 A1 | 10/2006 |
| JP | 7508444 A | 9/1995 |
| JP | 2001507599 A | 6/2001 |
| JP | 2003516173 A | 5/2003 |
| JP | 2003523784 A | 8/2003 |
| JP | 2004502490 A | 1/2004 |
| JP | 2004527287 A | 9/2004 |
| JP | 2006517824 A | 8/2006 |
| WO | WO99/42051 A1 | 8/1999 |
| WO | WO01/28442 A1 | 4/2001 |
| WO | WO02/03882 A2 | 1/2002 |
| WO | WO02/03882 A3 | 1/2002 |
| WO | WO02/051326 A1 | 7/2002 |
| WO | WO02/071960 A1 | 9/2002 |
| WO | WO03/045262 A2 | 6/2003 |
| WO | WO03/045262 A3 | 6/2003 |
| WO | WO2004/052246 A1 | 6/2004 |
| WO | WO2004/073532 A1 | 9/2004 |
| WO | WO2004/073533 A1 | 9/2004 |
| WO | WO2005/037150 A1 | 4/2005 |
| WO | WO2005/110258 A1 | 11/2005 |
| WO | WO2005/112835 A2 | 12/2005 |
| WO | WO2006/034423 A2 | 3/2006 |
| WO | WO2006/034423 A3 | 6/2006 |
| WO | WO2005/112835 A3 | 2/2008 |
| WO | WO2008/051423 A1 | 5/2008 |
| WO | WO2008/051801 A2 | 5/2008 |
| WO | WO2008/051801 A3 | 5/2008 |
| WO | WO2008/051802 A2 | 5/2008 |
| WO | WO2008/051806 A2 | 5/2008 |
| WO | WO2009/149407 A9 | 12/2009 |
| WO | WO2010/028165 A8 | 3/2010 |
| WO | WO2010/121256 A1 | 10/2010 |

OTHER PUBLICATIONS

Al Baz et al.; Modified Technique of Tension Band Wiring in Flexion Injuries of the Middle and Lower Cervical Spine; SPINE; vol. 20; No. 11, pp. 1241-1244; Jun. 1, 1995.

Brinckmann et al.; Mechanical aspects of the lumbar spine; Musculoskeletal Biomechanics; Theime Stuttgart-New York; Chapter 11; pp. 105-128; Jan. 2002.

Dickman et al.; Comparative mechanical properties of spinal cable and wire fixation systems; Spine; vol. 22; No. 6; pp. 596-604; Mar. 15, 1997.

EPO; European search report dated Dec. 4, 2012 for EP Application No. 07844408.0; 4 pages.

(56) References Cited

OTHER PUBLICATIONS

EPO; European office action dated Jun. 4, 2010 for EP Application No. 07852824.7; 5 pages.
EPO; European office action dated Oct. 5, 2009 for EP Application No. 07852824.7; 5 pages.
EPO; search report dated Oct. 13, 2009 for EP Application No. 07863431.8; 3 pages.
EPO; European office action dated Jun. 4, 2010 for EP Application No. 07863431.8; 5 pages.
EPO; European search report dated Dec. 6, 2012 for EP Application No. 10765340.4, 4 pages.
EPO; European search report dated May 10, 2013 for EP Application No. 07854186.9; 5 pages.
EPO; Office action dated Feb. 4, 2011 for EP Application 07863431.8; 5 pages.
Frymoyer et al.; An overview of the incidences and costs of low back pain; Ortho. Clin. North Am.; vol. 22; No. 2; pp. 263-71; Apr. 1991.
Garner et al.; Development and preclinical testing of a new tension-band device for the spine: the loop system; European Spine Journal; vol. 11; supp. 2; pp. S186-191; Aug. 2002.
Hamblen, David L.; Symposium: Dynamic stabilization of the lumbar spine; Orthopaedics today international.; vol. 9; No. 3; pp. 1-17; Mar./ Apr. 2006.
Heller; Stability of different wiring techniques in segmental spinal instrumentation. An experimental study; Archives of Orthopedic and Trauma Surgery; vol. 117; No. 1-2; pp. 96-99; Jan. 1998.
International Search Report and Written Opinion of PCT App. No. PCT/US2007/08185 dated Jan. 25, 2008; 10 pages.
International Search Report and Written Opinion of PCT App. No. PCT/US2007/022191 dated Mar. 14, 2008.
International Search Report and Written Opinion of PCT App. No. PCT/US2007/081835 dated Mar. 24, 2008.
International Search Report and Written Opinion of PCT/US2007/081822 dated May 8, 2008.
ISR and Written Opinion of PCT App. No. PCT/US2010/031615, dated Jun. 18, 2010, 9 pgs.
ISR and Written Opinion of PCT App. No. PCT/US2010/031471, dated Jul. 8, 2010, 13 pgs.
Leahy et al.; Design of spinous process hooks for flexible fixation of the lumbar spine; Proceedings of the Institution of Mechanical Engineers, Part H; Journal of Engineering in Medicine; vol. 214; No. 5; pp. 479-487; Sep. 27, 2000.
Leahy et al.; Mechanical testing of a flexible fixation device for the lumbar spine; Proceeding of the Institution of Mechanical Engineers, Part H; Journal of Engineering in Medicine; vol. 214; No. 5; pp. 489-495; Sep. 27, 2000.
Medtronic Sofamor Danek USA, Inc.; DIAM system implants; Product brochure; 20 pgs.; (year of pub. sufficiently earlier than effective US filed and any foreign priority date) 2005-2006.
Minns et al.; Preliminary design and experimenatal studies of a novel soft implant for correcting sagittal plane instability in the lumbar spine; Spine; vol. 22; No. 16; pp. 1819-1825; Aug. 15, 1997.
Moll et al.; Normal range of spinal mobility; Ann. Rheum. Dis; vol. 30; pp. 381-387; Mar. 1971.
Miyasaka et al.; Radiographic analysis of lumbar motion in relation to lumbosacral stability: Investigation of moderate and maximum motion; Spine; vol. 25; No. 6; pp. 732-737; Mar. 15, 2000.
Papp et al.; An in vitro study of biomechanical effects of flexible stabiliation on the lumbar spine; Spine; vol. 22; No. 2; pp. 151-155; Jan. 15, 1997.
Shepard et al.; Spinous process strength; Spine; vol. 25; No. 3; pp. 319-323; Feb. 1, 2000.
Shepard et al.; Slippage of a spinous process hook during flexion in a flexible fixation system for the lumbar spine; Medical Engineering and Physics; vol. 23; No. 2; pp. 135-141; Mar. 2001.
Voydeville et al.; Ligamentoplastie intervertebrale avec cale souple dans les instabilities lombaries; <<Intervertebral ligamentoplasty with flexible wedge in lumbar instability>>; Orthop. Traumatol.; vol. 2; pp. 259-264; Jan. 1992.
White et al.; Clinical biomechanics of the spine; vol. 2..; Philadelphia; Lippincott; Jan. 1990.
USPTO; Office action dated Apr. 20, 2010 for U.S. Appl. No. 11/777,366; 12 pages.
USPTO; Office action dated Oct. 12, 2010 for U.S. Appl. No. 11/777,366; 12 pages.
USPTO; Notice of Allowance dated May 5, 2011 for U.S. Appl. No. 11/777,366; 8 pages.
USPTO; Office action dated Jan. 29, 2013 for U.S. Appl. No. 11/827,980; 11 pages.
USPTO; Office action dated May 10, 2011 for U.S. Appl. No. 11/827,980; 10 pages.
USPTO; Office action dated Aug. 2, 2012 for U.S. Appl. No. 11/827,980; 9 pages.
USPTO; Office action dated Dec. 1, 2010 for U.S. Appl. No. 11/827,980; 10 pages.
USPTO; Notice of Allowance dated May 13, 2013 for U.S. Appl. No. 11/827,980; 6 pages.
USPTO; Office action dated Apr. 24, 2012 for U.S. Appl. No. 11/875,674; 15 pages.
USPTO; Office action dated Jun. 10, 2011 for U.S. Appl. No. 11/875,674; 15 pages.
USPTO; Office action dated Jun. 19, 2012 for U.S. Appl. No. 11/875,674; 19 pages.
USPTO; Office action dated Oct. 4, 2011 for U.S. Appl. No. 11/875,674; 18 pages.
USPTO; Office action dated Oct. 23, 2012 for U.S. Appl. No. 11/875,674;18 pages.
USPTO; Office action dated Jan. 20, 2012 for U.S. Appl. No. 12/106,049; 20 pages.
USPTO; Office action dated Mar. 19, 2013 for U.S. Appl. No. 12/106,049; 20 pages.
USPTO; Office action dated Aug. 5, 2011 for U.S. Appl. No. 12/106,049; 23 pages.
USPTO; Office action dated Oct. 2, 2012 for U.S. Appl. No. 12/106,049; 22 pages.
USPTO; Office action dated Jun. 13, 2011 for U.S. Appl. No. 12/426,119; 16 pages.
USPTO; Notice of Allowance dated Dec. 27, 2011 for U.S. Appl. No. 12/426,119; 5 pages.
USPTO; Office action dated May 13, 2011 for U.S. Appl. No. 12/426,167; 13 pages.
USPTO; Office action dated Oct. 17, 2011 for U.S. Appl. No. 12/426,167; 17 pages.
USPTO; Notice of Allowance dated Jan. 25, 2012 for U.S. Appl. No. 12/426,167 10 pages.
USPTO; Office action dated May 31, 2012 for U.S. Appl. No. 13/206,339; 23 pages.
USPTO; Office action dated Oct. 31, 2012 for U.S. Appl. No. 13/206,339; 16 pages.
USPTO; Notice of Allowance dated Feb. 5, 2013 for U.S. Appl. No. 13/206,339; 8 pages.
USPTO; Notice of Allowance dated Apr. 19, 2013 for U.S. Appl. No. 13/206,339; 2 pages.
USPTO; Office Action dated Sep. 30, 2014 for U.S. Appl. No. 13/274,171; 6 pages.
USPTO; Notice of Allowance dated Jun. 10, 2014 for U.S. Appl. No. 13/427,551; 8 pages.
USPTO; Office action dated Mar. 5, 2013 for U.S. Appl. No. 13/455,917; 14 pages.
USPTO; Office action dated Oct. 29, 2012 for U.S. Appl. No. 13/455,917; 13 pages.
USPTO; Office Action dated Apr. 6, 2015 for U.S. Appl. No. 13/889,581; 16 pages.
USPTO; Notice of Allowance dated Nov. 20, 2015 for U.S. Appl. No. 13/889,581; 6 pages.
USPTO; Office Action dated Jul. 14, 2014 for U.S. Appl. No. 13/958,323; 8 pages.
USPTO; Office Action dated Nov. 13, 2014 for U.S. Appl. No. 13/958,323; 9 pages.
USPTO; Notice of Allowance dated May 28, 2015 for U.S. Appl. No. 13/958,323; 5 pages.

(56) References Cited

OTHER PUBLICATIONS

USPTO; Office Action dated Jul. 20, 2016 for U.S. Appl. No. 14/875,495.
USPTO; Office Action dated Aug. 26, 2016 for U.S. Appl. No. 15/053,924; 8 pages.
International Preliminary Report on Patentability of PCT App. No. PCT/US2007/081815 dated Apr. 22, 2009; 8 pages.
USPTO; Office Action dated Aug. 7, 2017 for U.S Appl. No. 15/442,503; 8 pages.
Alamin et al.; U.S. Appl. No. 15/805,554 entitled "Methods and systems for laterally stabilized constraint of spinous processes," filed Nov. 7, 2017.

* cited by examiner

METHODS AND SYSTEMS FOR CONSTRAINT OF SPINOUS PROCESSES WITH ATTACHMENT

CROSS REFERENCE TO RELATED APPLICATIONS

This application is a continuation of U.S. patent application Ser. No. 14/875,495, filed on Oct. 5, 2015, Publication No. US-2016-0256201-A1, which is a continuation of U.S. patent application Ser. No. 13/958,323, filed on Aug. 2, 2013, now U.S. Pat. No. 9,149,304, which is a continuation of U.S. patent application Ser. No. 11/827,980, filed on Jul. 13, 2007, now U.S. Pat. No. 8,523,904, which claims the benefit of U.S. Provisional Patent Application No. 60/862,085, filed on Oct. 19, 2006, each of which is herein incorporated by reference in its entirety.

U.S. patent application Ser. No. 11/827,980 is also a continuation-in-part of U.S. patent application Ser. No. 11/076,469, filed on Mar. 9, 2005, now U.S. Pat. No. 7,458,981, which claimed the benefit of U.S. Provisional Patent Application No. 60/551,235, filed on Mar. 9, 2004, each of which is herein incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

BACKGROUND OF THE INVENTION

1. Field of the Invention

The present invention relates generally to medical methods and apparatus. More particularly, the present invention relates to methods and devices for restricting spinal flexion in patients having back pain or other spinal conditions.

A major source of chronic low back pain is discogenic pain, also known as internal disc disruption. Patients suffering from discogenic pain tend to be young, otherwise healthy individuals who present with pain localized to the back. Discogenic pain usually occurs at the discs located at the L4-L5 or L5-S1 junctions of the spine (FIG. 1). Pain tends to be exacerbated when patients put their lumbar spines into flexion (i.e. by sitting or bending forward) and relieved when they put their lumbar spines into extension (i.e. arching backwards). Discogenic pain can be quite disabling, and for some patients, can dramatically affect their ability to work and otherwise enjoy their lives.

This pain experienced by patients with discogenic low back pain can be thought of as flexion instability, and is related to flexion instability that is manifested in other conditions. The most prevalent of these is spondylolisthesis, a spinal condition in which abnormal segmental translation is exacerbated by segmental flexion. The device described here should as such also be useful for these other spinal disorders associated with segmental flexion, for which the prevention or control of spinal segmental flexion is desired.

Current treatment alternatives for patients diagnosed with chronic discogenic pain are quite limited. Many patients follow a conservative treatment path, such as physical therapy, massage, anti-inflammatory and analgesic medications, muscle relaxants, and epidural steroid injections, but typically continue to suffer with a significant degree of pain.

Other patients elect to undergo spinal fusion surgery, which commonly requires discectomy (removal of the disk) together with fusion of adjacent vertebra. Fusion is not usually recommended for discogenic pain because it is irreversible, costly, associated with high morbidity, and of questionable effectiveness. Despite its drawbacks, however, spinal fusion for discogenic pain remains common due to the lack of viable alternatives.

Recently, a less invasive and potentially more effective treatment for discogenic pain has been proposed. A spinal implant has been designed which inhibits spinal flexion while allowing substantially unrestricted spinal extension. The implant is placed over one or more adjacent pairs of spinal processes and provides an elastic restraint to the spreading apart of the spinal processes which occurs during flexion. Such devices and methods for their use are described in U.S. Patent Application Publication No. 2005/02161017A1, published on Sep. 29, 2005, and having common inventors with the present application.

As illustrated in FIG. 2, an implant 10 as described in the '017 application, typically comprises an upper strap component 12 and a lower strap component 14 joined by a pair of compliant members 16. The upper strap 12 is shown disposed over the top of the spinous process SP4 of L4 while the lower strap 14 is shown extending over the bottom of the spinous process SP5 of L5. The compliance member 16 will typically include an internal element, such as a spring of rubber block, which is attached to the straps 12 and 14 in such a way that the straps may be "elastically" or "compliantly" pulled apart as the spinous processes SP4 and SP5 move apart during flexion. In this way, the implant provides an elastic tension on the spinal processes which provides a force that resists flexion. The force increases, typically linearly with a non-variable spring constant, as the processes move further apart. Usually, the straps themselves will be essentially non-compliant so that the degree of elasticity or compliance may be controlled and provided solely by the compliance members 16.

Although providing significant benefits, the system illustrated in FIG. 2 can be difficult to implant in certain patient anatomies where the spinous processes are relatively small or have certain geometries. Moreover, the systems are not intended for implantation at the L5-S1 junction as the spinous process on the sacrum is not always sufficient for attachment with this system.

For these reasons, it would be desirable to provide improved spinal implants and methods for their use for inhibiting flexion in patients suffering from discogenic pain. It would be particularly desirable if the improved implants and methods would be suitable for implantation at the L5-S1 junction and in patients having anatomies which prevent other difficulties for implantation of the prior systems as described in the '017 application. At least some of these objectives will be met by the inventions described hereinbelow.

2. Description of the Background Art

US 2005/0216017A1 has been described above. Other patents and published applications of interest include: U.S. Pat. Nos. 4,966,600; 5,011,494; 5,092,866; 5,116,340; 5,282,863; 5,395,374; 5,415,658; 5,415,661; 5,449,361; 5,456,722; 5,462,542; 5,496,318; 5,540,698; 5,609,634; 5,645,599; 5,725,582; 5,902,305; Re. 36,221; 5,928,232; 5,935,133; 5,964,769; 5,989,256; 6,053,921; 6,312,431; 6,364,883; 6,378,289; 6,391,030; 6,468,309; 6,436,099; 6,451,019; 6,582,433; 6,605,091; 6,626,944; 6,629,975; 6,652,527; 6,652,585; 6,656,185; 6,669,729; 6,682,533; 6,689,140; 6,712,819; 6,689,168; 6,695,852; 6,716,245;

6,761,720; 6,835,205; Published U.S. patent application Nos. US 2002/0151978; US 2004/0024458; US 2004/0106995; US 2004/0116927; US 2004/0117017; US 2004/0127989; US 2004/0172132; US 2005/0033435; US 2005/0049708; US 2006/0069447; Published PCT Application Nos. WO 01/28442 A1; WO 02/03882 A2; WO 02/051326 A1; WO 02/071960 A1; WO 03/045262 A1; WO 2004/052246 A1; WO 2004/073532 A1; and Published Foreign Application Nos. EP 0322334 A1; and FR 2 681 525 A1.

BRIEF SUMMARY OF THE INVENTION

The present invention provides spinal implants and methods for restricting spinal flexion for the treatment of discogenic pain and other spinal conditions, such as spondylolisthesis, in which the physician may desire to control segmental flexion. The methods comprise positioning a first segment of a tether structure over a spinous process of a vertebra without attachment. At least one other segment of the tether structure is attached to an adjacent vertebra or sacrum, and at least a portion of the tether structure is adapted to elastically elongate to apply tension between the spinous process and the adjacent vertebra or sacrum as the spine undergoes flexion, i.e., as the spinous process moves apart from the adjacent vertebra or sacrum as the patient leans forward. The methods and implants of the present invention are particularly useful for treating the L4-L5 and the L5-S1 junctions of the spine (FIG. 1). The first segment of the tether structure is generally a loop similar or identical to strap 12 in FIG. 1 which is non-fixedly attached to a spinous process, typically being placed over a superior spinous process but not being otherwise attached to the spinous process. Thus, the first segment of the tether will be able to move or shift laterally and/or in the anterior-posterior direction relative to the spinous process as the spine undergoes flexion and extension.

The at least one other segment of the tether may be attached to the adjacent vertebra or sacrum in a variety of ways. In a first group of embodiments, the at least one other segment of the tether structure will be fixedly attached to the adjacent vertebra or sacrum so that the segment will not move relative to a point of attachment. For example, the other segment of the tether structure may comprise two separate end segments which are fixedly attached to the vertebra or sacrum, for example with screws, dowels, staples, pins, sutures, or the like. When attached to a vertebra, the two separate end segments may be attached to opposed sides of a spinous process on an inferior vertebra. When attached to a sacrum, the two separate end segments may be attached to an alar surface of the sacrum, typically with alar screws.

In a second set of embodiments, the at least one other segment of the tether structure may be non-fixedly attached to the adjacent vertebra or sacrum so that the segment can move or shift relative to a point of attachment. For example, the at least one other segment may comprise a loop similar to the lower strap 14 of FIG. 2. A hole may be formed in the spinous process of an adjacent vertebra so that the loop may be passed through the hole to provide a non-fixed attachment. Similarly, a hole could be formed in a protruding surface structure on the sacrum to receive the lower loop segment of the tether structure. Alternatively, such a loop segment could be passed through the eye(s) of one or more islet screws which are implanted into the lower vertebra or sacrum.

The tether structure will typically comprise at least one compliance member and more typically comprise two compliance members, generally as described in connection with the embodiment in FIG. 2. When the tether structure comprises at least two compliance members, there will be at least one loop segment or strap extending between the upper ends of the compliance members. The strap will usually be non-compliant but could in other embodiments have a limited compliance or flexibility. The tether structure may comprise a further lower loop segment or strap, generally as illustrated in FIG. 2, when the tether structure is intended to pass through an islet or hole in the lower vertebra or sacrum. Alternatively, the tether structure will comprise at least two additional segments having separate ends which extend from each of the two compliance members. The separate ends will be adapted for anchoring to the adjacent vertebra or sacrum using screws, dowels, staples, or any of the techniques described above.

In all cases, the tether structure will typically provide little or no restriction or resistance to extension of the spine. Most often, the tether structure will be free from components or other structures which are located between the adjacent spinous processes or between the spinous processes and the adjacent sacrum. In other instances, however, a cross-member or other low profile structure may be placed between the two compliance members to maintain alliance of the compliance members, generally as described in co-pending application Ser. No. 11/777,366, filed on the same day as the present application. The use of cross-members for stabilizing the compliance members may be advantageous when the lower portion of the tether structure is non-fixedly attached to the lower vertebra or sacrum.

In a further aspect of the present invention, a spinal implant comprises at least two compliance members, where each compliance member has an upper and a lower end. An upper tether structure extends between the upper ends of the two compliance members and is adapted for placement over a spinous process of a first vertebra. Typically, the upper tether structure will be a non-compliant strap. The spinal implant further comprises a first lower tether structure attached at an upper end to the lower end of the compliance member and having a lower end adapted to be fixedly attached to a vertebra or sacrum adjacent to the first vertebra. A second lower tether segment is attached at its upper end to a lower end of the second compliance member and has a lower end adapted to be fixedly attached to the vertebra or sacrum adjacent to the first vertebra. The lower ends of the first and second lower tether segments are typically non-compliant straps and may be adapted to be screwed into the adjacent vertebra or sacrum. Alternatively, the lower ends of the first and second lower tether segments may be adapted to be attached to a dowel implanted in the adjacent vertebra or sacrum. The spinal implant may optionally comply to screws, anchors, or other attachment members for fixedly attaching the lower ends of the tether segments to the vertebra or sacrum.

DETAILED DESCRIPTION OF THE INVENTION

Figure 1:
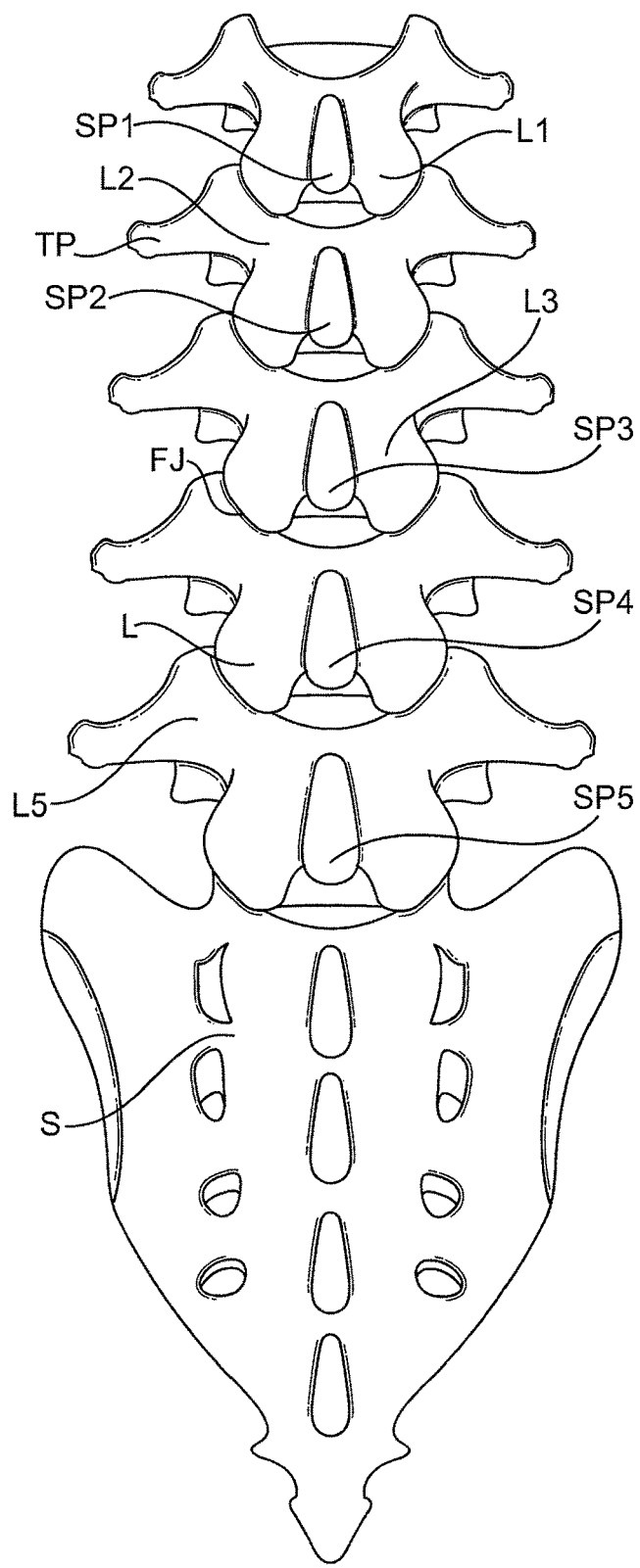
FIG. 1 is a schematic diagram illustrating the lumbar region of the spine including the spinous processes (SP), facet joints (FJ), lamina (L), transverse processes (TP), and sacrum (S).
Figure 2:
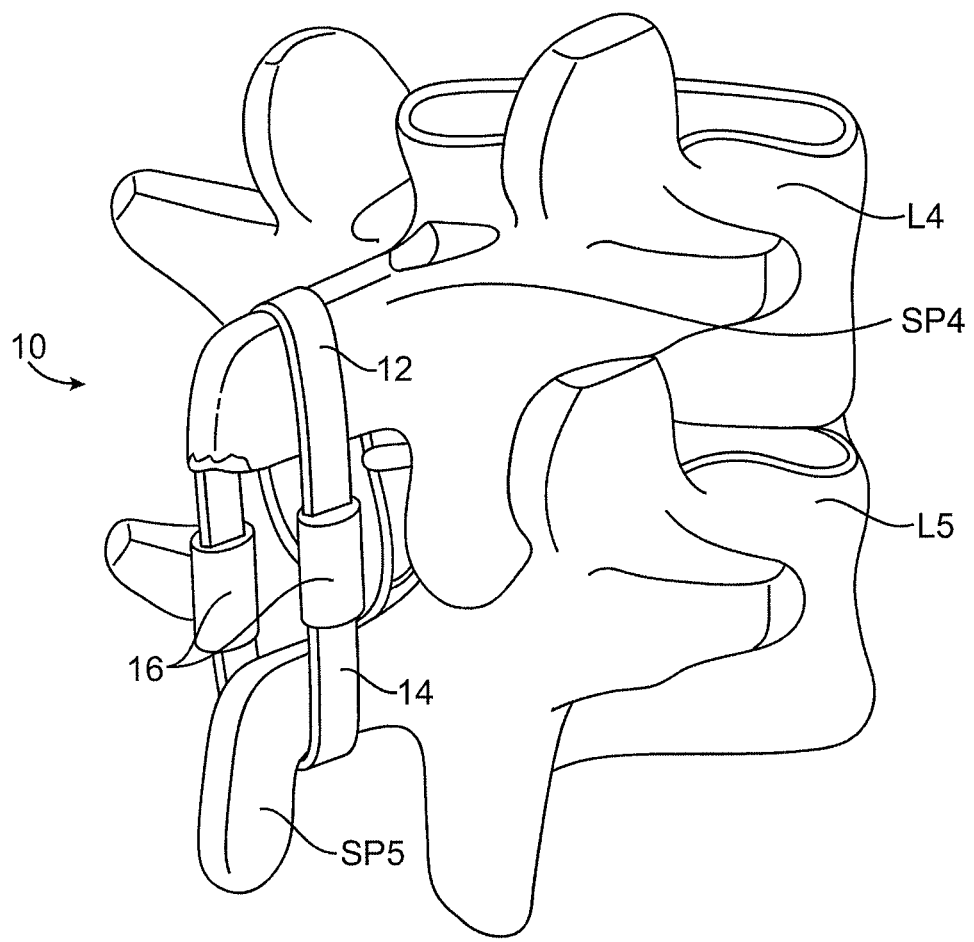
FIG. 2 illustrates a spinal implant of the type described in US 2005/0216017A1.
Figure 3:
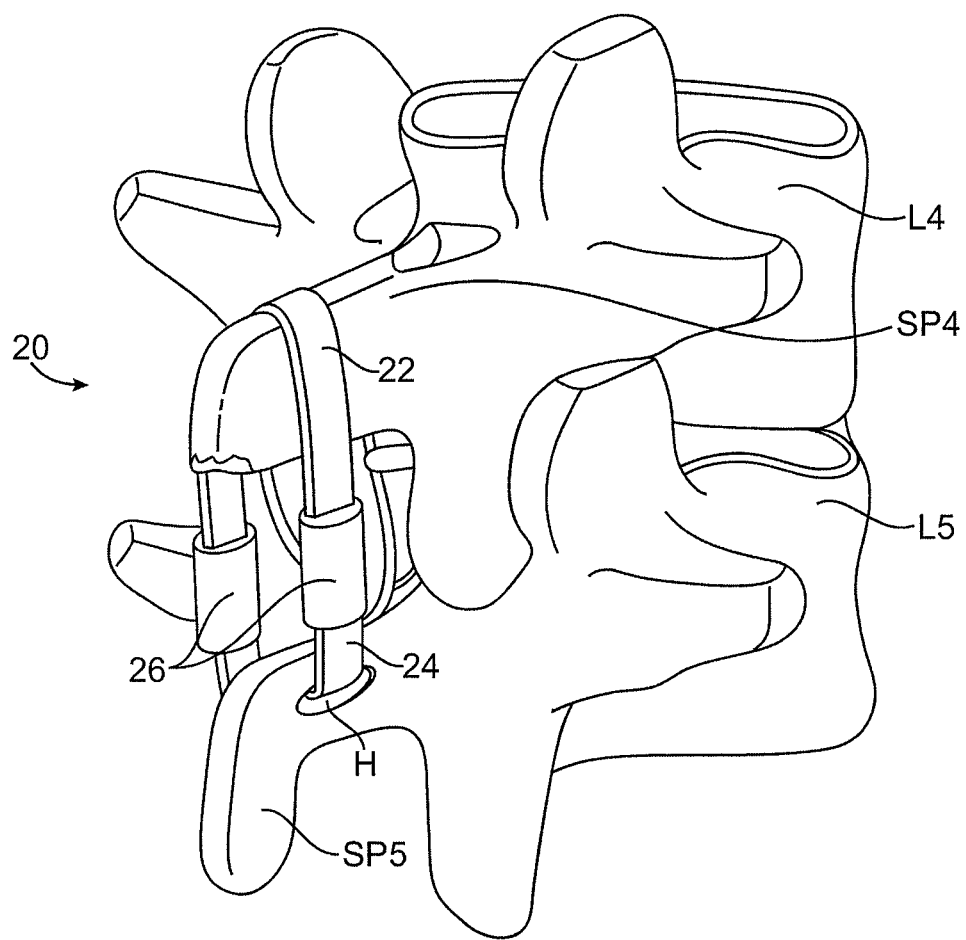
FIG. 3 illustrates a first embodiment of a spinal implant adapted to be placed between a pair of spinous processes and having a lower tether segment non-fixedly attached to the lower spinous process.

Referring now to FIG. 3, a spinal implant 20 suitable for use in accordance with the methods of the present invention comprises an upper strap 22, a lower strap 24, and a pair of compliance members 26 joining the upper and lower straps. Typically, the upper and lower straps 22 and 24 will be non-distensible but will be joined to the compliance members 26 so that they can be expanded from a constricted configuration, as shown in broken line, when the patient's spine is in a neutral position between flexion and extension, to an expanded configuration (shown in full line) when the patient's spine is in flexion. The compliance members 26 will provide a force which acts against the extension of the spinous processes SP4 and SP5, as generally described in prior patent application U.S. 2005/0216017, which has been previously incorporated herein by reference. In contrast to the teachings of the '017 application, however, the lower strap 24 is non-fixedly attached to the spinous process SP5 of L5. By passing through a hole H formed in the spinous process SP5, the lower strap 24 is maintained stably and will not be displaced.

Figure 4:
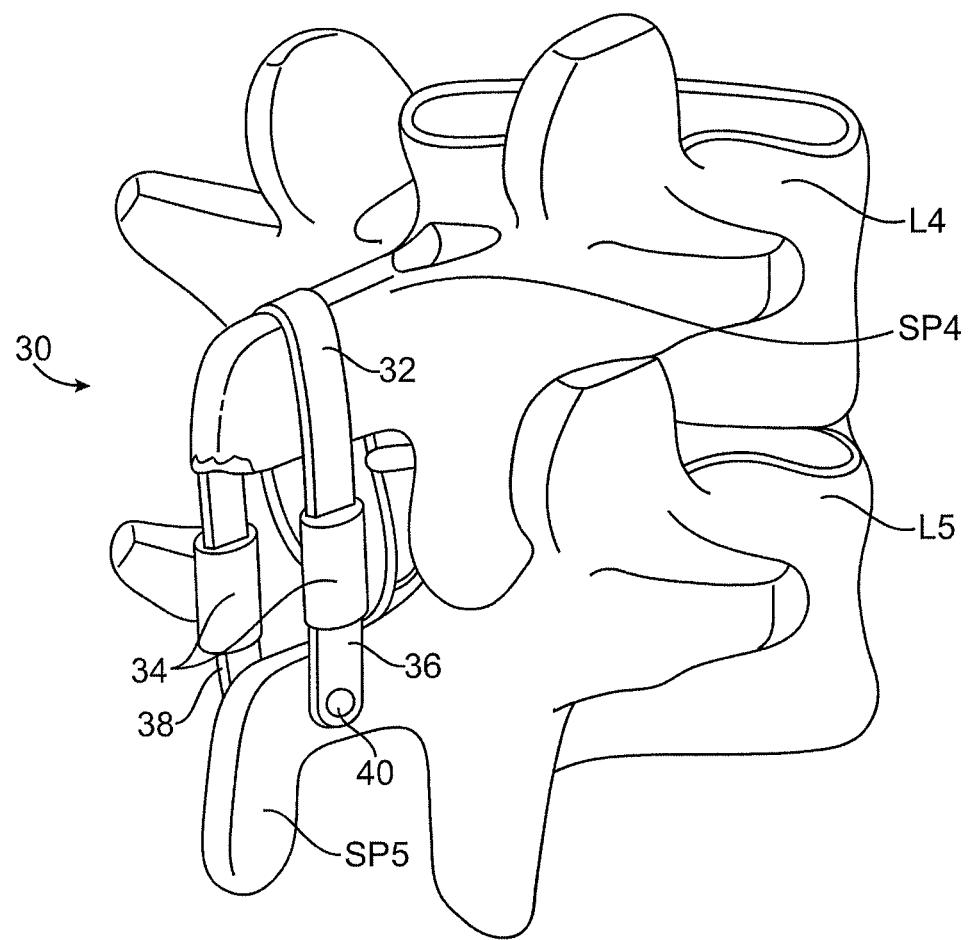
FIG. 4 is a second embodiment of a spinal implant adapted to be placed between adjacent spinous processes and having a lower segment adapted to be fixedly attached to the lower spinous process.

Referring now to FIG. 4, a spinal implant 30 may comprise a tether structure including an upper strap 32, a pair of compliance members 34, and first and second lower straps 36 and 38, one strap extending from each of the compliance members 34. The lower straps 36 will typically be non-compliant, as is the upper strap 32, with the compliance and elasticity being provided by compliance members 34. The lower ends of the lower straps 36 and 38 may be fixedly attached to the spinous process SP5 using screws 40 or any other suitable anchors. By using the screw or other anchors, the lower straps 36 and 38 will be fixedly attached to the spinous process SP5, permitting no relative movement between the straps 36 and 38 and the spinous process SP5 and L5. The upper strap 32, in contrast, will be able to move or shift slightly relative to the upper spinous process SP4 on L4, although the interspinous ligament that stretches between L4 and L5 (through which the strap passes) will resist motion in the anterior-posterior direction.

Figure 5:
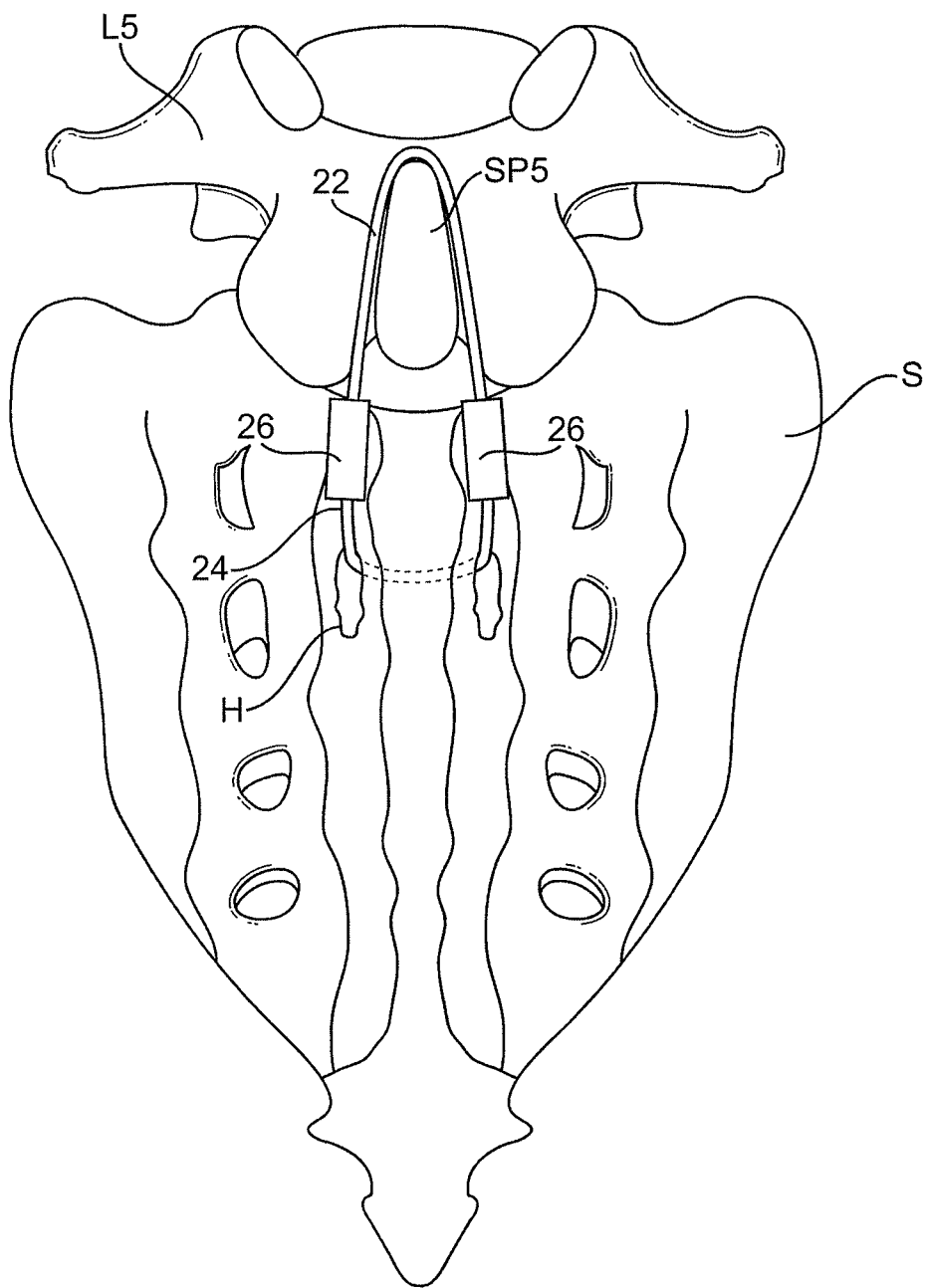
FIG. 5 illustrates a third embodiment of a spinal implant according to the present invention having an upper end placed over the spinous process of L5 and a lower end non-fixedly attached to the sacrum.

Referring now to FIG. 5, the spinal implant 20, generally described in FIG. 3, may also be implanted between the spinous process SP5 of L5 and the sacrum S. The upper strap 22 will be placed over spinous process SP5 while the lower strap 24 will be placed through a hole H placed in a surface ridge on the dorsal surface of the sacrum.

Figure 6:
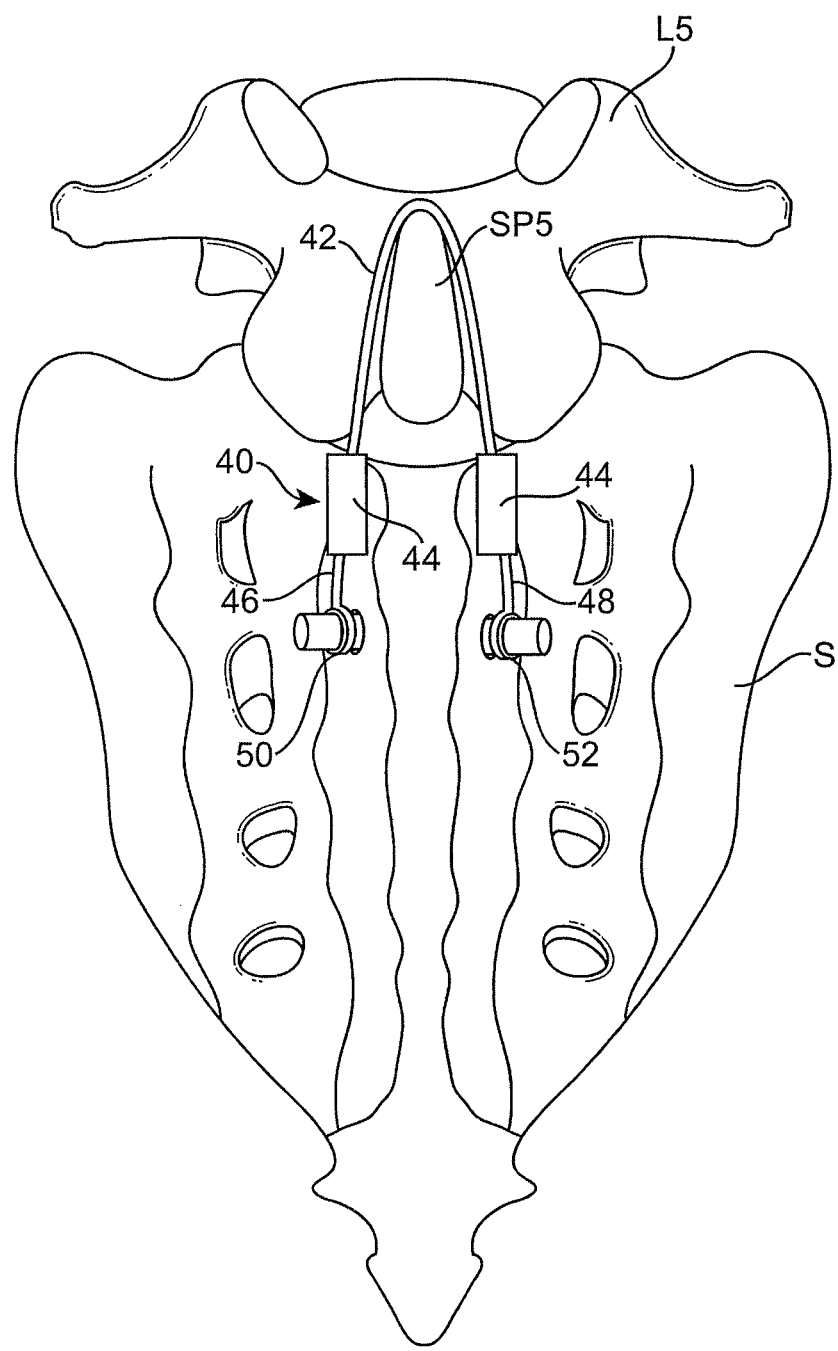
FIG. 6 illustrates a fourth embodiment of a spinal implant according to the present invention having an upper end secured over a spinous process of L5 and two separate lower segments attached to a dowel implanted in the sacrum.

Referring now to FIG. 6, a spinal implant 40 comprising an upper strap 42, a pair of compliance members 44 and lower strap segments 46 and 48 may be implanted over the spinous process SP5 of L5 and the sacrum S. In particular, a dowel or other anchor element may be implanted in the S1 spinous process of the sacrum (which is typically small relative to the L5 spinous process and less able to provide an anchor around which a strap can be looped) and rings 50 and 52 at the lower ends of the lower strap segments 46 and 48 may be placed over the dowel or other anchor.

Figure 7:
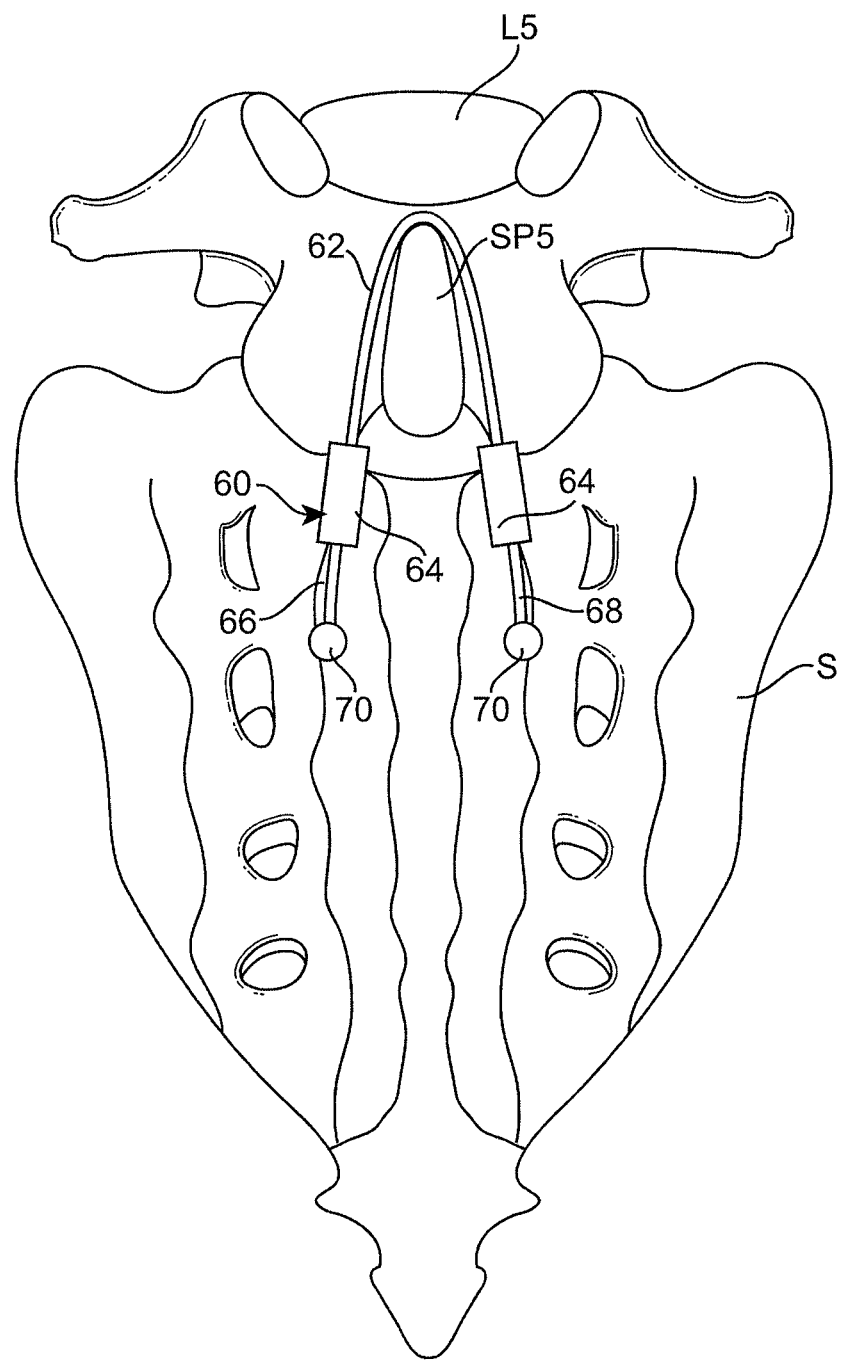
FIG. 7 illustrates a fifth embodiment of a spinal implant according to the present invention having an upper segment placed over a spinous process of L5 and two separate lower segments fixedly attached by alar screws to the sacrum.

As illustrated in FIG. 7, a further alternative for implanting an implant 60 is illustrated. Implant 60 comprises an upper strap 62, a pair of compliance members 64 and lower strap segments 66 and 68. The upper strap segment is placed over spinous process SP5 of L5 while the lower strap segments 66 and 68 are anchored on the alar region of the sacrum by alar screws 70.

Figure 8:
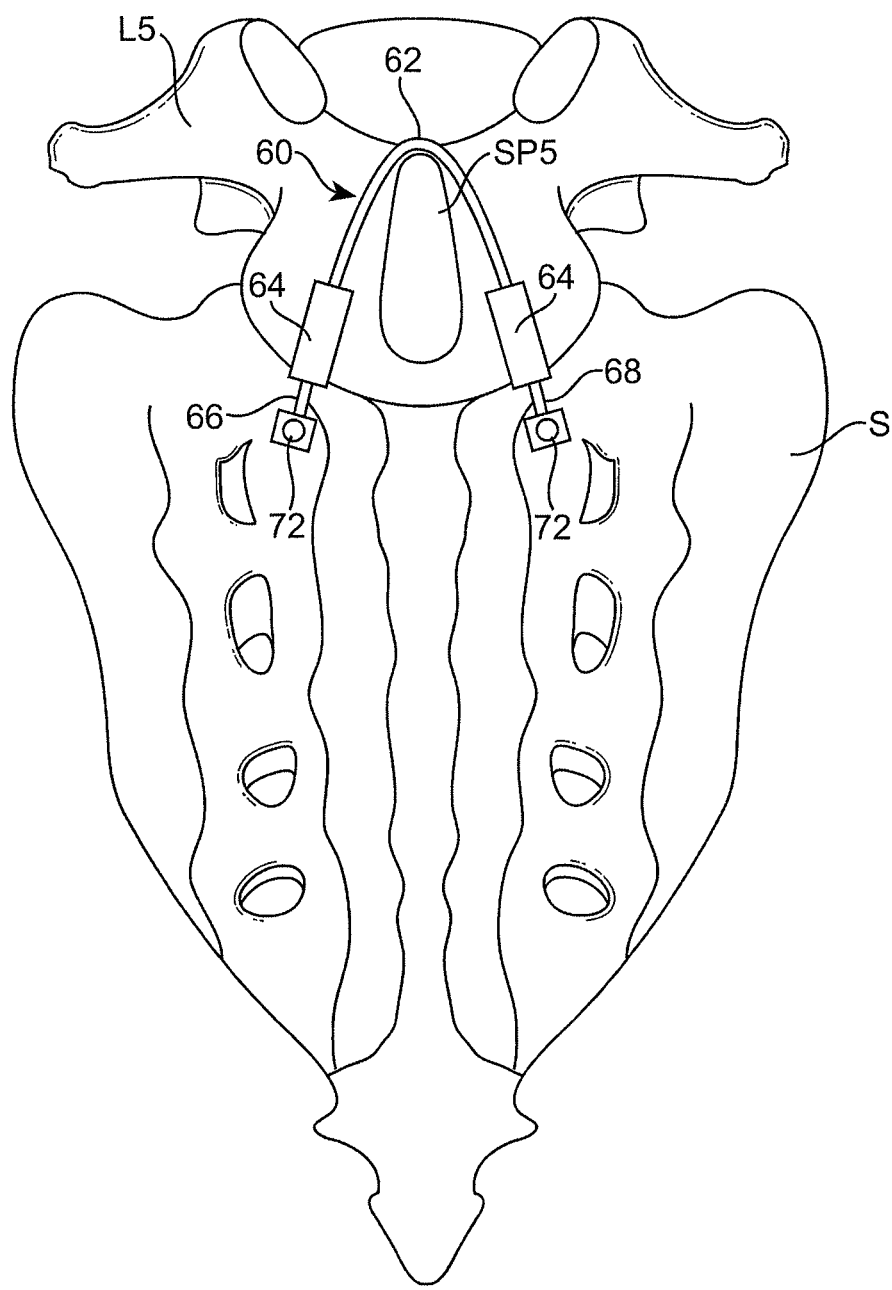
FIG. 8 illustrates a sixth embodiment of a spinal implant according to the present invention having an upper segment placed over a spinous process of L5 and two separate lower segments fixedly attached by superior articular facet screws to the sacrum.

As illustrated in FIG. 8, a further alternative for implanting an implant 60 is illustrated. Implant 60 comprises an upper strap 62, a pair of compliance members 64 and lower strap segments 66 and 68. The upper strap segment is placed over spinous process SP5 of L5 while the lower strap segments 66 and 68 are anchored to superior articular facets of the sacrum by superior articular facet screws 72.

Figure 9:
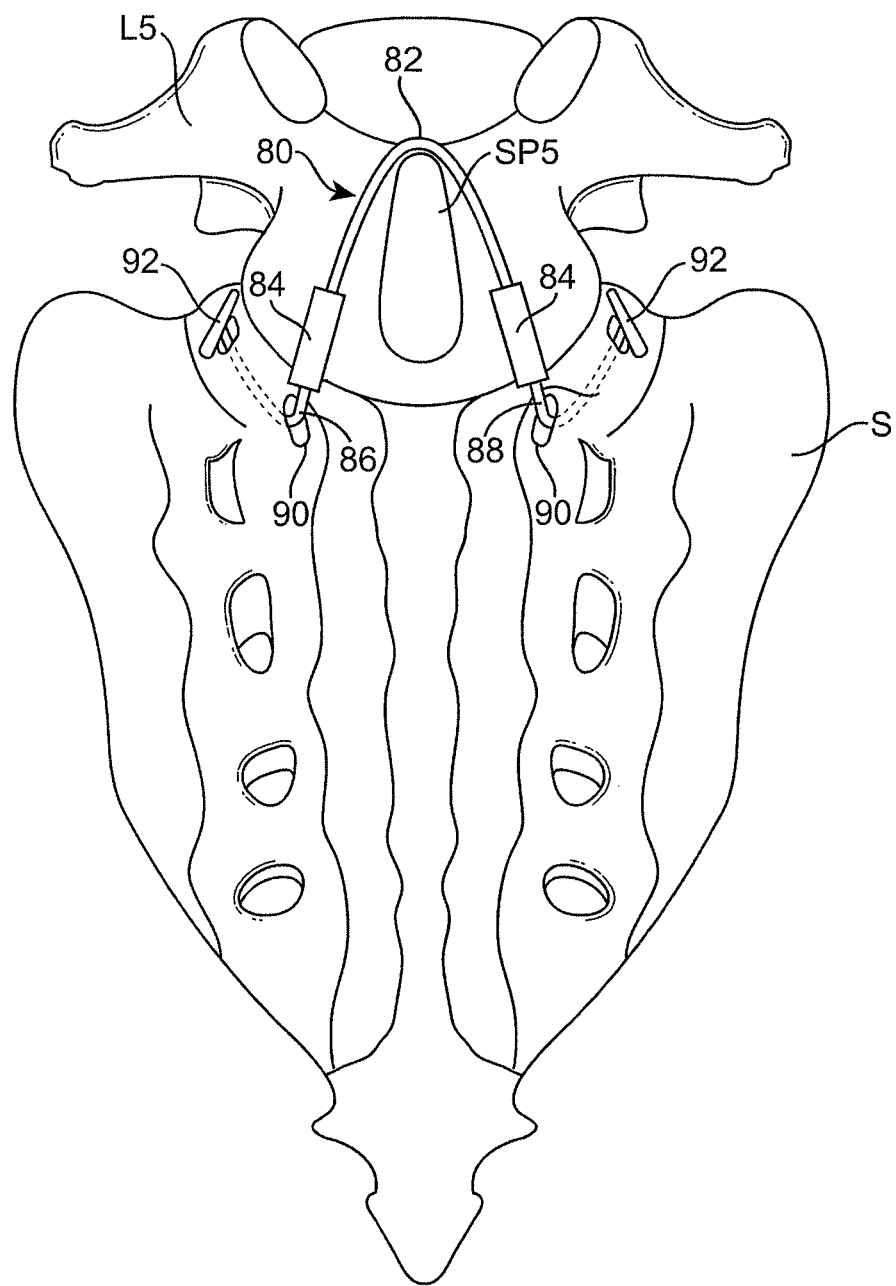
FIG. 9 illustrates a seventh embodiment of a spinal implant according to the present invention having an upper segment placed over a spinous process of L5 and two separate lower tether segments each of which passes through a hole created in the superior articular facet of S1 and is non-fixedly attached via a toggle anchor (t-anchor).

As illustrated in FIG. 9, a further alternative for implanting an implant 80 is illustrated. Implant 80 comprises an upper strap 82, a pair of compliance members 84 and lower strap segments 86 and 88. The upper strap segment is placed over spinous process SP5 of L5 while the lower strap segments 86 and 88 pass dorsal-medial to proximal-lateral through holes 90 created in the superior articular facet of S1 and are non-fixedly attached via toggle anchors (t-anchors) 92 on the proximal-lateral side of the facets.

Figure 10:
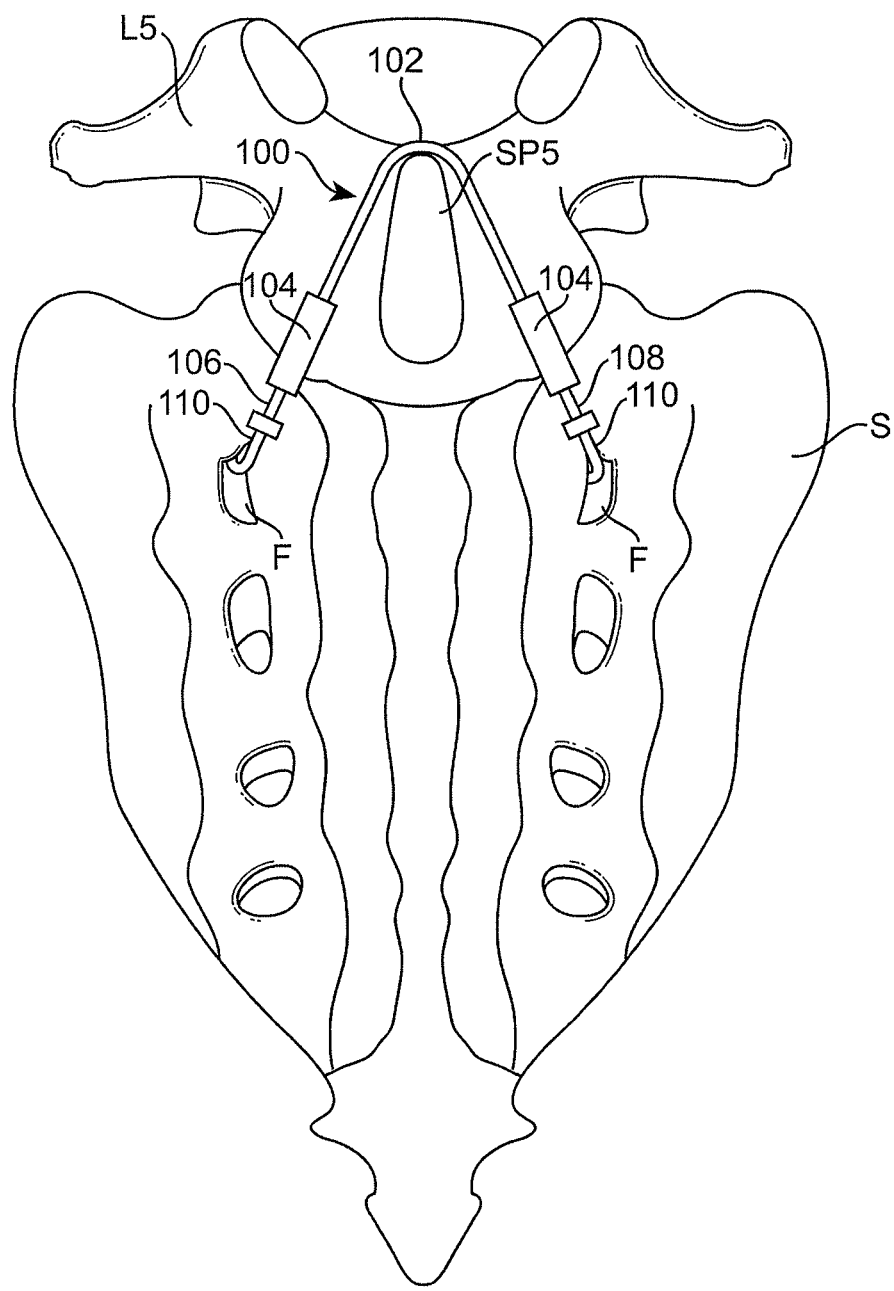
FIG. 10 illustrates an eighth embodiment of a spinal implant according to the present invention having an upper segment placed over a spinous process of L5 and two separate lower tether segments each of which is connected to a hook attached to the dorsal S1 foramen.

As illustrated in FIG. 10, a further alternative for implanting an implant 100 is illustrated. Implant 100 comprises an upper strap 102, a pair of compliance members 104 and lower strap segments 106 and 108. The upper strap segment is placed over spinous process SP5 of L5 while the lower strap segments 106 and 108 are connected to hooks 110 attached to the dorsal S1 foramen F.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for restricting flexion of a spine, said method comprising:
   positioning a structure over a spinous process of a vertebra without attachment;
   attaching the structure to a first end of at least one separate compliance member; and
   attaching a second end of the at least one separate compliance member to an adjacent vertebra or sacrum with one or more anchors so that said second end will be fixed at a point of attachment;

wherein the compliance member elastically elongates to controllably restrict flexion of the vertebra relative to the adjacent vertebra or sacrum;

wherein positioning comprises positioning a first segment of the structure over the spinous process of a vertebra without attachment and attaching at least one other segment of the structure to the adjacent vertebra or sacrum, wherein the first segment and the at least one other segment of the structure each have an end segment which is fixedly attached to the adjacent vertebra or sacrum wherein the end segments are attached to opposed sides of a spinous process.

2. A method as in claim 1, wherein the end segments are attached to opposed sides of a spinous process with screws or dowels.

3. A method as in claim 1, wherein the end segments are attached to an alar surface of the sacrum.

4. A method as in claim 1, wherein positioning comprises positioning the first segment of the structure over a spinous process of L4 and attaching comprises attaching the at least one other segment to L5.

5. A method as in claim 1, wherein positioning comprises positioning the first segment of the structure over a spinous process of L5 and attaching comprises attaching the at least one other segment to the sacrum.

6. A method as in claim 1, wherein the first and at least one other segment of the structure are non-compliant and do not substantially elongate in response to flexion of the spine.

7. A method as in claim 1, wherein the segments of the structure are attached by at least two compliance members which are disposed on opposite sides of the spinous processes.

8. A method as in claim 1, wherein the structure provides no substantial restriction to extension of the spine.

9. A method as in claim 8, wherein the structure is free from components placed between adjacent spinous processes or a spinous process and an adjacent sacrum.

10. A method as in claim 1, wherein the structure comprises a tether structure.

* * * * *